United States Patent
Hughes et al.

(10) Patent No.: US 7,153,497 B2
(45) Date of Patent: Dec. 26, 2006

(54) CONTROLLED DISSOLUTION OF ACTIVE INGREDIENTS

(75) Inventors: Lyn Hughes, Harleysville, PA (US);
Simon Andrew Bellamy, Redhill (GB);
Christina Hann, Gwynedd, PA (US)

(73) Assignee: Rohm and Haas Company, Philadelphia, PA (US)

( * ) Notice: Subject to any disclaimer, the term of this patent is extended or adjusted under 35 U.S.C. 154(b) by 77 days.

(21) Appl. No.: 10/107,898

(22) Filed: Mar. 26, 2002

(65) Prior Publication Data

US 2002/0146384 A1      Oct. 10, 2002

Related U.S. Application Data

(60) Provisional application No. 60/282,443, filed on Apr. 9, 2001.

(51) Int. Cl.
*A61K 31/74* (2006.01)
*A61K 31/785* (2006.01)
*A61K 9/14* (2006.01)

(52) U.S. Cl. ............... 424/78.1; 424/78.11; 424/78.16; 424/486

(58) Field of Classification Search .............. 424/78.1, 424/78.16, 78.11, 486
See application file for complete search history.

(56) References Cited

U.S. PATENT DOCUMENTS 4,133,696 A * 1/1979 Barker et al. .............. 127/46.2
4,510,128 A * 4/1985 Khanna ................... 424/78.16
4,898,729 A * 2/1990 Miller et al. .............. 424/78.11
5,811,436 A   9/1998 Leonard et al. ............. 514/321

FOREIGN PATENT DOCUMENTS

EP       0391518 B1     10/1990
WO    WO 91/13612    *  9/1991
WO    WO9211001         9/1992

OTHER PUBLICATIONS

Advanced Analytical Biochemistry ion Exchange Chromatography; Principles and Applications of High Performance Ion-Exchange Chromatography for bioseparations from The separations Group, Hesperia, CA, USA (1998).*
Basic principles in ion exchange chromatogrphy from the Amersha, biosciences group.*
Pope et al., "Oral Controlled-Release Delivery of Ivermectin In Cattle via an Osmotic Pump", Journal of Pharmaceutical Sciences, vol. 74, No. 10, pp. 1108-1110, 1985.
Theeuwes et al., "Elementary Osmotic Pump of Indomethacin", Journal of Pharmaceutical Sciences, vol. 72, No. 3, pp. 253-258, 1983.
Conte et al., "Compressed Barrier Layers for Constant Drug Release from Swellable Matrix Tablets", S.T.P. Pharma Sciences 4 (2) 107-113, 1994.
Kim et al., "Release Kinetics of Coated, Donut-Shaped Tablets for Water Soluble Drugs", European Journal of Pharmaceutical Sciences, 9, 237-242, 1999.

(Continued)

*Primary Examiner*—Michael G. Hartley
*Assistant Examiner*—Blessing Fubara
(74) *Attorney, Agent, or Firm*—Kenneth Crimaldi; Joanne P. Will

(57) ABSTRACT

A dosage form comprising a resin/resinate combination is described. Said dosage form allows optimization of the release rate profile of active ingredients.

12 Claims, 7 Drawing Sheets

OTHER PUBLICATIONS

Ganlin et al., "The Kinetics of Nimodipine Release from Swellable Hydrophilic Matrix", Journal of Chinese Pharmaceutical Sciences, 9 (2), 104-107, 2000.

Sriwongjanya M et al; "Effect of ion exchange resins on the drug release from matrix tablets"; European Journal of Pharmaceutics and Biopharmaceutics, Elsevier Science Publishers B.V., Amsterdam, NL; vol. 46, No. 3; pp. 321-327.

Konar N et al; "Water-Soluble Polycations as Oral Drug Carriers (Tablets)"; Journal of Pharmaceutical Sciences, American Pharmaceutical Association. Washington, US'; vol. 86, No. 12; pp. 1339-1344.

Ichikawa Hideki et al; "Use of Ion-Exchange Resins to prepare 100 mum-sized microcapsules with prolonged drug-release by the Wurster process."; International Journal of Pharmaceutics (Kidlington); vol. 216, No. 1-2, pp. 67-76; 2001.

Lele B S et al; "Mucoadhesive drug carriers based on complexes of poly (acrylic acid) and PEGylated drugs having hydrolysable PEG-anhyddride-drug linkages"; Journal of Controlled Release, Elsevier Science Publishers B.V. Amsterdam, NL: vol. 69, No. 2; pp. 237-248.

* cited by examiner

CONTROLLED DISSOLUTION OF ACTIVE INGREDIENTS

CROSS REFERENCE TO RELATED PATENT APPLICATIONS

This is a non-provisional application of prior pending U.S. provisional application Ser. No. 60/282,443 filed Apr. 9, 2001.

BACKGROUND OF THE INVENTION

The concept of controlled, extended, or modified release of biologically active ingredients is well known, and can be very advantageous in the administering of said active ingredients. For example, in the area of pharmaceuticals, by extending the release of a pharmaceutically active ingredient it is possible to increase the time during which the blood plasma concentration of said active ingredient is between an upper limit, defined by the toxicological properties of said active ingredient and a lower limit defined by the efficacy of the said active ingredient. Particularly desirable are constant release rate and delayed release. Additionally, in the area of water treatment chemicals, controlled release can result in the more efficient use of the active ingredient because similar limits exist where the upper limit is defined by processing requirements, such as limiting corrosion and reducing toxicity to non-targeted organisms, and the lower limit is defined by efficacy. Further in the area of agricultural chemicals, controlled release is beneficial because similar limits exist where the upper limit is defined by pollution of the environment, and toxicity to non-targeted organisms, and the lower limit is defined by efficacy.

There are many examples of different methods known in the industry for modifying the release rate of active ingredients, including many commercialized formulations. One of the methods that has been used in the pharmaceutical art is to convert the drug active ingredient into a complex with an ion exchange resin to form a resinate. Resinates are salts formed between ion exchange resins and ionizable active ingredients. Cation exchange resins form resinates with basic active ingredients. Anion exchange resins form resinates with acidic active ingredients. In the resinate the active ingredient and the resin are in their ionized forms. When resinates are exposed to fluids such as physiological fluids the active ingredient can be released from the resinate by the mechanism of ion exchange. The rate of release of active ingredients from resinates depends on several factors which are well known in the industry. These include, but are not limited to, degree of cross-linking of the ion exchange resin, the particle size of the resinate, the pK of the functional groups of the resin, the solubility of the active ingredient in the release fluid, the ionic strength and pH of the release fluid, the pK of the active ingredient, the molecular weight of the active ingredient, and the temperature. Coating the resin with a permeable membrane can also change the rate of release. Coating the resin with non-permeable membranes can change the conditions under which the release takes place depending on the conditions under which the membrane dissolves.

Using the variables described above, the resinate can be used to provide some control of the release rate, providing an extended release of the active ingredient. Because of the nature of the mechanism, resinates give a fast release to start, when the concentration of the active ingredient in the resinate is high, followed by a gradually reducing release rate as the concentration of active ingredient decreases. Because of this it has been a problem in the art of ion exchange resinate technology to achieve constant release or delayed release. Thus, the application of ion exchange resinate technology as a means of delivering active ingredients has been limited.

The art has attempted to achieve constant release rates and delayed release without the use of ion exchange resins. The osmotic pump (D. G. Pope et al, Journal of Pharmaceutical Sciences, Volume 74, pages 1108–1110. F Theeuwes et al, Journal of Pharmaceutical Sciences, Volume 72, pages 253–258) achieves this by using osmotic pressure to eject the active substance from the device at a constant rate. This method can also be used to achieve delayed release. Another method used is the erodable tablet (U.S. Pat. No. 4,525,345. C. Kim et al, European Journal of Pharmaceutical Sciences Volume 7, pages 237–242) where the rate of erosion of the tablet is used to control the rate of release of the active substance. This method can also be used to achieve delayed release. A third method is the use of swellable polymeric matrices (G. Zao et al, Journal of Chinese Pharmaceutical Science, Volume 9, pages 104–107. U. Conte et al, S. T. P. Pharma Sci, Volume 4, pages 107–110) where the rate of swelling and diffusion control the rate of release. However, these methods are not applicable to all active ingredients or applications.

Thus, there is a need for alternative methods for controlling the release rates of active ingredients. Applicants have surprisingly discovered resinate/unloaded resin compositions for delivering active ingredients, exhibiting constant release rate and delayed release profiles. Thus, Applicants' invention solves the problems in the resinate art.

The following terms have the following meanings herein:

The term "release rate profile", as used herein, means the rate at which the substance that is loaded on the resin appears in solution in the release medium. This can be expressed in terms of the instantaneous concentration of the substance in solution as a function of time, or expressed in terms of the percentage of total substance available that has appeared in solution in the release medium as a function of time.

The term "release medium" and as used herein, means the liquid medium into which the substances is being released. Examples of release media can be water, simulated intestinal fluid, simulated gastric fluid, simulated saliva, or the authentic physiological versions of these fluids, water, and various buffer solutions.

The term "ion exchange resin", as used herein, means any insoluble polymer that can act as an ion exchanger.

The term "release", as used herein, means the transfer of substance from the resinate into the release medium. When applied to a resin or resinate, the term "absorption", as used herein, means the reverse of release, namely the transfer of substance from the medium into the ion exchange resin or resinate.

The term "water retention capacity" as used herein is used to describe the maximum amount of water that an ion exchange resin can retain within the polymer phase and in any pores. (ASTM D2187: Standard Test Methods for Physical and Chemical Properties of Particulate Ion Exchange Resin. Test Method B: Water Retention Capacity)

The term "resinate," as used herein, means a complex formed between an active ingredient and an ion exchange resin. It is also known as a loaded resin. The term "resinate" can also be expressed as an active ingredient/ion exchange resin complex.

Further, ion exchange resins are characterized by their capacity to exchange ions. This is expressed as the "Ion Exchange Capacity." For cation exchange resins the term used is "Cation Exchange Capacity," and for anion exchange resins the term used is "Anion Exchange Capacity." The ion exchange capacity is measured as the number equivalents of an ion that can be exchanged and can be expressed with reference to the mass of the polymer (herein abbreviated to "Weight Capacity") or its volume (often abbreviated to "Volume Capacity"). A frequently used unit for weight capacity is "milliequivalents of exchange capacity per gram of dry polymer." This is commonly abbreviated to "meq/g."

Ion exchange resins are manufactured in different forms. These forms can include spherical and non-spherical particles with size in the range of 0.00001 mm to 2 mm. The non-spherical particles are frequently manufactured by grinding of the spherical particles. Products made in this way typically have particle size in the range 0.0001 mm to 0.2 mm. The spherical particles are frequently known in the art as 'Whole Bead.' The non-spherical particles are frequently known in the art as 'Powders.'

STATEMENT OF THE INVENTION

Figure 1:
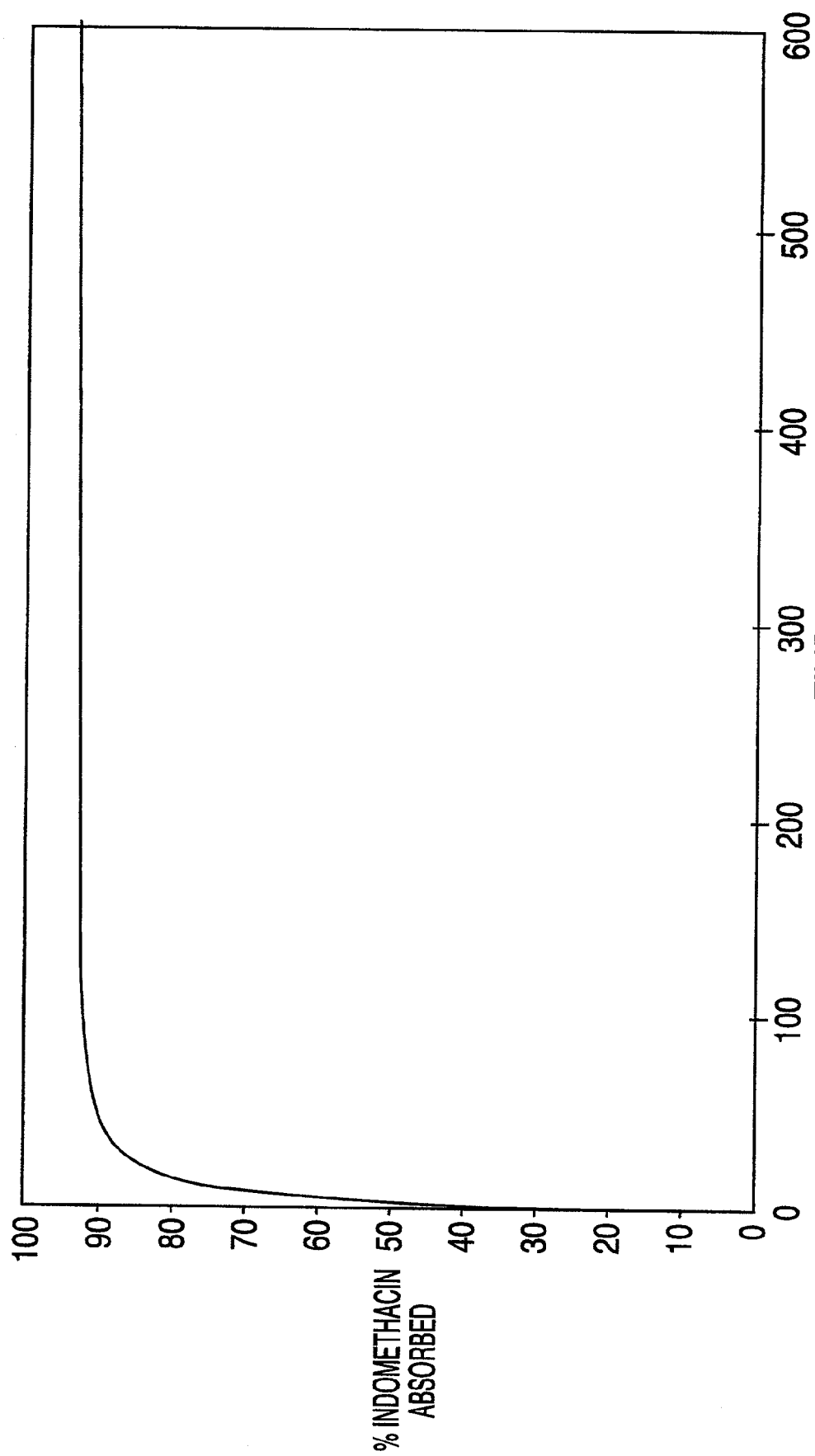
FIG. 1 is a graph showing the absorption of indomethacin by cholestyramine based on the data from Example 1.

The present invention relates to the use of ion exchange polymers to control the rate at which active ingredients are released into solution. Specifically, the present invention relates to a dosage form comprising:
a. an active ingredient/ion exchange resin complex wherein said active ingredient is ionizable; and
b. an unloaded ion exchange resin

DETAILED DESCRIPTION OF THE INVENTION

The present invention relates to a dosage form comprising:
a. an active ingredient/ion exchange resin complex wherein said active ingredient is ionizable; and
b. an unloaded ion exchange resin In the present invention an unloaded resin (b.) is administered at the same time as a resinate of an active ingredient (a.). The combination of the unloaded resin and the resinate creates a release rate profile that is different from the profile created by administering resinate alone. For example, by suitable manipulation of the composition the release rate can be made to be approximately constant over several hours, or the time to maximum release rate can be delayed significantly relative to using resinate alone.

Ion exchange resins useful in the practice of the present invention include, but are not limited to, anionic exchange resins and cationic exchange resins. Preferably, said resins are suitable for human and animal ingestion when the application is pharmaceutical.

Preferred anionic exchange resins include, but are not limited to, styrenic strongly basic anion exchange resins with a quaternary amine functionality having a weight capacity of 0.1 to 15 meq/g, and styrenic weakly basic anion exchange resins with a primary, secondary, or tertiary amine functionality having a weight capacity of 0.1 to 8.5 meq/g, and acrylic or methacrylic strongly basic anion exchange resins with a quaternary amine functionality having a weight capacity of 0.1 to 12 meq/g, and acrylic or methacrylic weakly basic anion exchange resins with a primary, secondary, or tertiary amine functionality having a weight capacity of 0.1 to 12 meq/g, and allylic and vinylic weakly basic anion exchange resins with a primary, secondary, or tertiary amine functionality having a weight capacity of 0.1 to 24 meq/g.

More preferred anionic exchange resins include, but are not limited to, styrenic strongly basic anion exchange resins with a quaternary amine functionality having a weight capacity of 0.1 to 6 meq/g, and styrenic weakly basic anion exchange resins with a tertiary amine functionality having a weight capacity of 0.1 to 8.5 meq/g, acrylic or methacrylic strongly basic anion exchange resins with a quaternary amine functionality having a weight capacity of 0.1 to 8 meq/g, and acrylic or methacrylic weakly basic anion exchange resins with a tertiary amine functionality having a weight capacity of 0.1 to 12 meq/g, and allylic and vinylic weakly basic anion exchange resins with primary, secondary, or tertiary amine functionalities having a weight capacity of 0.1 to 24 meq/g.

Most preferred anionic exchange resins include, but are not limited to, styrenic strongly basic anion exchange resins with a quaternary amine functionality with weight capacity of 0.1 to 6 meq/g and acrylic anion exchange resins with a tertiary amine functionality with weight capacity of 0.1 to 12 meq/g. Styrenic strongly basic anion exchange resins with quaternary amine functionalities with weight capacities of 4.0 to 4.5 meq/g are also known as cholestyramine resins.

Preferred cationic exchange resins include, but are not limited to, styrenic strongly acidic cation exchange resins with sulfonic or phosphonic acid functionalities having a weight capacity of 0.1 to 8 meq/g; and styrenic weakly acidic cation exchange resins with carboxylic or phenolic acid functionalities having a weight capacity of 0.1 to 8.5 meq/g; and acrylic or methacrylic weakly acidic cation exchange resins with a carboxylic or phenolic acid functionality with a weight capacity of 0.1 to 14 meq/g.

More preferred cationic exchange resins include, but are not limited to, styrenic strongly acidic cation exchange resins with a sulfonic acid functionality having a weight capacity of 0.1 to 8 meq/g; and styrenic weakly acidic cation exchange resins with a phenolic acid functionality having a weight capacity of 0.1 to 8.5 meq/g; and acrylic or methacrylic weakly acidic cation exchange resins with a carboxylic or phenolic acid functionality with a weight capacity of 0.1 to 14 meq/g.

Most preferred cationic exchange resins include, but are not limited to, styrenic strongly acidic cation exchange resins with a sulfonic acid functionality with a weight capacity of 0.1 to 8 meq/g, and acrylic or methacrylic weakly acidic cation exchange resin with a carboxylic acid functionality with weight capacity of 0.1 to 14 meq/g.

Ion exchange resins useful in this invention have a moisture content between 0% and the water retention capacity of said resin.

Ion exchange resins useful in this invention are in powder or whole bead form.

Strongly acidic and weakly acidic cation exchange resins useful in the practice of the present invention are in the acid form or salt form or partial salt form.

Strongly basic anion exchange resins useful in this invention are in the salt form.

Weakly basic anion exchange resins useful in this invention are in the free-base form or salt form or partial salt form.

The ratios of unloaded resin to resinate useful for this invention will be defined by the desired release rate profile. A typical ratio of unloaded resin to resinate is from 0.01 to 99. The preferred ratio is from 0.1 to 10. The most preferred ratio is from 0.2 to 5.

The particle size of resins and resinates useful in the invention will be defined by the desired release rate profile Typical particle sizes are from 0.00001 mm to 2 mm. The preferred size is 0.001 mm to 1 mm. The most preferred size is 0.001 mm to 1.0 mm Permeable coatings useful in this invention are well know to one skilled in the art and include Eudragit® RL100, and Eudragit® RS100 (Rohm-Pharma Darmstadt, Germany)

Non-permeable coatings useful in this invention are well known to one skilled in the art and include Aquacoat® CPD (FMC Corporation, Philadelphia, Pa., USA), Eudragit® E100, Eudragit® L100, Eudragit® S100 (Rohm-Pharma Darmstadt, Germany), Kollicoat® MA 30 DP (BASF Aktiengesellschaft, Ludwigshafen, Germany).

Active ingredients useful in the practice of the present invention include, but are not limited to, pharmaceutically active ingredients, vitamins, flavors, fragrances, water treatment chemicals such as dispersants, corrosion inhibitors, chelants, biocides, and scale inhibitors, and agricultural chemicals including pesticides, herbicides, fertilizers, and nutrients, that have acidic or basic ionizable groups.

Pharmaceutically active ingredients useful in the practice of this invention are those that include acidic or basic ionizable groups. Said pharmaceutically active ingredients include, but are not limited to, indomethacin, salicylic acid, ibuprofen, sulindac, diclofenac, piroxicam, naproxen, timolol, pilocarpine, acetylcholine, dibucaine, thorazine, promazine, chlorpromazine, acepromazine, aminopromazine, perazine, prochlorperazine, trifluoroperazine, thioproperazine, reserpine, deserpine, chlorprothixene, tiotixene, haloperidol, moperone, trifluorperidol, timiperone, droperidol, pimozide, sulpiride, tiapride, hydroxyzine, chlordiazepoxide, diazepam, propanolol, metoprolol, pindolol, imipramine, amitryptyline, mianserine, phenelzine, iproniazid, amphetamines, dexamphetamines, fenproporex, phentermine, amfepramone, pemoline, clofenciclan, cyprodenate, aminorex, mazindol, progabide, codergoctine, dihydroergocristine, vincamone, citicoline, physostigmine, pyritinol, meclofenoxate, lansoprazole, nifedipine, risperidone, clarithromycin, cisapride, nelfinavir, midazolam, lorazepam, nicotine, prozac, erythromycin, ciprofloxacin, quinapril, isotretinoin, valcyclovir, acyclovir, delavirdin, famciclovir, lamivudine, zalcitabine, osteltamivir, abacavir, prilosec, Vitamins useful in the practice of the present invention include, but are not limited to, A, C, E, and K.

Flavors and fragrances useful in the practice of the present invention include, but are not limited to, vanillin, methyl salicylate, thymol, ethyl vanillin, acesulfame, and saccharin.

Water treatment and detergent additive compounds useful in the practice of the present invention include, but are not limited to, polymers and copolymers of acrylic acid or methacrylic acid with other polymerizable monomers such as acrylamidomethyl propane sulfonic acid, ethyl acrylate, acrylamide and alkyl derivatives of acrylamide, allyl hydroxypropylether sulfonic acid, and their salts used as dispersants and scale inhibitors, phosphonate compounds such as 1-hydroxyethilidene-1,1-diphosphonic acid, aminotris(phosphonic acid), phosphonobutane tricarboxylic acid, and hydroxyphosphonoacetic acid, used as scale inhibitors or corrosion inhibitors, aminotris(acetic acid) and ethylene diamine tetraacetic, used as chelants, quaternary nitrogen compounds such as alkyldimethylbenzylammonium chloride, used as biocides.

Agricultural compounds useful in the practice of the present invention include, but are not limited to, ferbam, fosetyl-aluminum, glufosinate, glyphosate, pesticides that contain carboxyl groups, such as (2,4-dichlorophenoxy) acetic acid, 4-chloro-2-methylphenoxybutyric acid, 4-chloro-2-methylphenoxyacetic acid, herbicides such as diphenylethers and the dithiocarbamates, and pesticides that contain amino groups.

The active ingredient component of the composition may be present in any amount which is sufficient to elicit a beneficial effect. Preferably, the loading of active ingredient in the resinate of the present invention is 1–100% of the ion exchange capacity of the resin, more preferably it is 5–95% of the ion exchange capacity of the resin, most preferably it is 10–90% of the ion exchange capacity of the resin.

The preferred temperature range for the practice of the present invention is −10° C. to 150° C., the more preferred range is 0° C. to 100° C., the even more preferred range is 5° C. to 60° C., and the most preferred range is 5° C. to 50° C.

While not wishing to be bound by theory, Applicants propose that a release/absorption/re-release process is occurring. For example, when the present invention is used in the pharmaceutical arts, a mixture of an unloaded ion exchange resin (b.) and a resinate (a.) are exposed to the release medium such as intestinal fluid, the active ingredient starts to be released from the resinate (a.). A part of this released active ingredient is absorbed by the resin (b.) because the system attempts to achieve equilibrium. The active ingredient that is absorbed by the unloaded resin (b.) is not, therefore, absorbed by the body at this stage. The released part that is not absorbed by the unloaded resin (b.) is absorbed by the body, causing, by law of mass action, further active ingredient to be released from the resinate (a.), some of which is then absorbed by the, now partially loaded, resin (b.). This process continues until the amount of active ingredient on the unloaded resin (b.) is in equilibrium with the active ingredient in solution. After this point further decrease in the concentration of the active ingredient by absorption into the body will result in the unloaded resin (b.) starting to release the active ingredient it has previously absorbed.

The unloaded resin (b.) must be chosen such that under conditions of use a significant amount of the active ingredient in solution is absorbed by the unloaded resin. Current understanding in the industry does not permit prediction a priori of the types of unloaded resin/active ingredient combinations that fulfill this requirement. The suitable resin/active ingredient combination can be determined by techniques known to those skilled in the art. For example, one can measure the uptake of the active ingredient by the unloaded resin from a solution of the active ingredient in the release medium using a simple spectrophotometric absorption analysis as described herein. The spectrophotometric data can serve as a guide to selecting appropriate resin/active ingredient combinations.

The resinate (a.) can be any combination of active ingredient and ion exchange resin that forms a stable resinate, and releases said active ingredient when exposed to the release fluid. Current understanding in the industry does not permit prediction a priori of the types of resin/active ingredient combinations that are required to form a useful resinate. However, it can be determined by techniques known to those skilled in the art. For example, one can prepare a resinate and test the release of the active ingredient in an appropriate release medium using a simple spectrophotometric absorption analysis as described herein.

The final formulation of the mixture can be any of the many variations known in the art, provided that they do not result in transfer of the active ingredient from the resinate into the unloaded resin during storage and prior to use. These can include, but are not limited to, tablets, powders, pills, syrups, hard capsules and soft capsules.

The unloaded resin (b.) and the resinate (a.) do not have to be mixed in the formulation. In those cases where the resin and resinate are mixed prior to use, any of the known methods for preparing mixtures of solids can be used in the practice of this invention. See, Remington's Pharmaceutical Sciences, 16$^{th}$ Edition, 1980, Chapter 88.

The invention is not restricted to the use of only one unloaded resin with only one resinate, multiple resinates and/or multiple unloaded resins can also be used as needed to produce the desired release rate profile.

It is not necessary that the ion exchange resin used in the preparation of the resinate be of the same type as used for the unloaded resin.

The rate of release of active ingredients from resinates, or absorption of active ingredients onto unloaded resins depend on multiple factors which are well known in the industry. These include, but are not limited to, degree of cross-linking of the ion exchange resin, the particles size of the resinate, the pK of the functional groups of the resin, the solubility of the active ingredient in the fluid, the ionic strength and pH of the fluid, the pK of the active ingredient, the molecular weight of the active ingredient, and the temperature. Coating the unloaded resin or resinate with a permeable membrane can also change the rate of release or absorption. Coating the unloaded resin or resinate with non-permeable membranes can change the conditions under which the release and absorption takes place depending on the conditions under which the membrane dissolves. Methods for selecting and using coatings are very well known in the art. See, Remington's Pharmaceutical Sciences, 16$^{th}$ Edition, 1980, Chapter 91.

By balancing the variables that control the rate of release from the resinate, rate of absorption by the unloaded resin and subsequent rate of rerelease, the shape of the release rate curve can be modified. For example, small reductions in the curvature of the profile can be obtained by small amounts of absorption/release. Increasing the amount of absorption/release can result in a profile that is almost linear for extended periods. A linear profile is equivalent to a constant release rate, a highly desirable profile. Non-limiting examples are provided herein below.

EXAMPLE 1

Spectrophotometric Absorption Test Method

It is important that the drug be absorbed by the resin. The following test method is useful in determining drug absorption by the resin. In this illustration of the test method, indomethacin and cholestyramine are used. A 50 ml continuous, stirred, filtration cell, the Amicon stirred ultrafiltration cell model 8050, available from Millipore Corporation, was equipped with a peristaltic pump to feed fluid into the cell at a rate in the range 3–10 ml/min. The filtrate from the cell was passed into a 1 cm path length flow-through quartz uv cell. The uv cell was situated in a suitable uv spectrophotometer, the Genesys 2, UV Spectrophotemer available from Spectronic Instruments. The effluent from the uv cell was supplied back to the pump, such that the fluid was continuously circulated through the filtration cell and uv cell. The filtration cell was fitted with a 3 micron filter to retain the resin particles. 55 ml of a 98 mg/l solution of indomethacin in simulated intestinal fluid, prepared as described below, was charged to the filtration cell and the pump and stirrer started. Flow rate was approximately 6 ml/min. Absorbance readings were taken on the uv spectrophotometer at a wavelength of 318 nm until a steady baseline was obtained. 43 mg of Cholestyramine USP that had been screened to remove particles <75 microns was then added to the cell. Absorbance readings were then taken at frequent intervals to observe the uptake of indomethacin. The absorbance readings were used to calculate the indomethacin concentration from a suitably determined calibration curve. The results of the experiment are shown in FIG. 1, expressed as % of indomethacin absorbed. This example illustrates that the unloaded ion exchange resin absorbs indomethacin active ingredient from simulated intestinal fluid.

EXAMPLE 2

Preparation of Indomethacin/Cholestyramine Resinate 2.01 g of Cholestyramine USP was added to 1000 ml of 6% sodium bicarbonate solution, and the slurry mixed for 1 hour. The slurry was filtered through a 3 micron filter and the resin washed twice with 150 ml of deionized water. The wetcake was added to a solution of 1.00 g indomethacin dissolved in 100 ml of 50% aqueous ethanol. This mixture was shaken overnight and then filtered using a 3 micron filter. The wetcake was washed once with 100 ml of deionized water. The indomethacin solution filtrate and the water wash were combined and the indomethacin concentration determined from the absorbance at a wavelength of 320 nm. The indomethacin loading was calculated to be 0.128 g/g of wet resinate. Cholestyramine USP is a styrenic strongly basic anion exchange resin with a quaternary amine functionality having a weight capacity of 4.0 to 4.5 meq/g.

EXAMPLE 3

Preparation of Diclofenac/Cholestyramine Resinate 0.92 g of of Cholestyramine USP that had been screened to remove particles <75 microns was added to 74.8 g of deionized water in a 200 ml screw-topped glass container. 1.00 g of diclofenac sodium was then added and the mixture shaken overnight. The mixture was then filtered and the solid washed with approximately 30 ml of water. The amount of combined filtrate was 110 ml. The wt of solid (the resinate) was 2.31 g. The filtrate was diluted and the diclofenac concentration determined from the absorbance at a wavelength of 276 nm. The concentration in the filtrate was found to be 311 mg/l expressed as diclofenac sodium. Based on these data the loading of diclofenac sodium in the resinate was calculated to be 0.418 g/g wet resinate.

EXAMPLE 4

Release Test on Diclofenac/Cholestyramine Resinate

Figure 2:
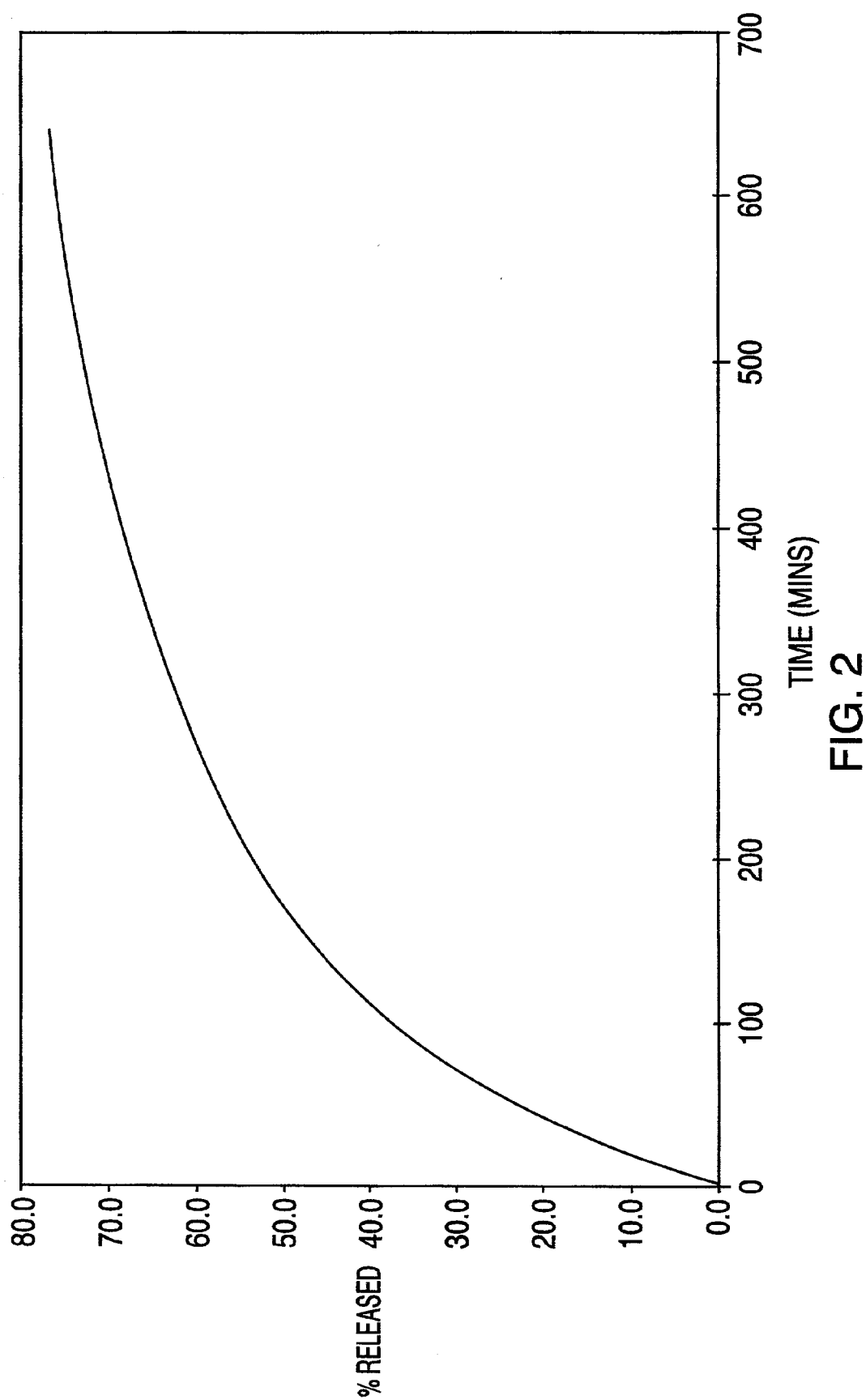
FIG. 2 is a graph showing the release of diclofenac from a resinate based on the data from Example 4.
Figure 3:
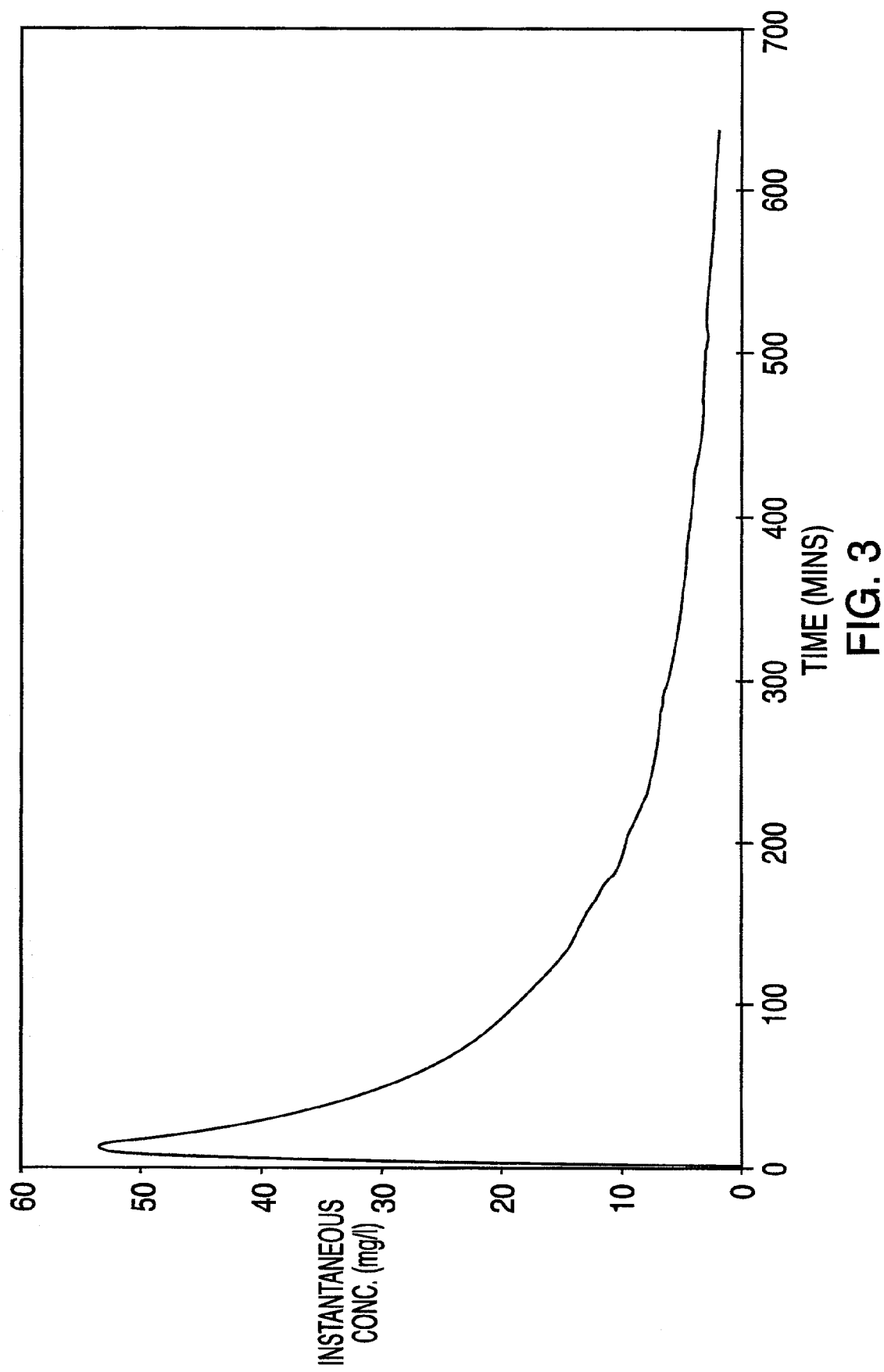
FIG. 3 is a graph showing the release of diclofenac from a resinate based on the data from Example 4.

The equipment used was the same as that described in Example 1 except that it was not operated as a circulating system. Instead, simulated intestinal fluid was supplied to the pump at a flow rate of 6.4 ml/min, and the effluent from the uv cell was directed to waste. 122.8 mg of the wet resinate prepared as in Example 3 was added to the filtration cell. The uv spectrophotomer was operated at a wavelength of 276 nm and the diclofenac sodium concentration was calculated using a suitably determined calibration curve. The results of this example as shown in FIG. 2 expressed as % diclofenac sodium released, and in FIG. 3 expressed as the instantaneous concentration in the effluent. The example illustrates the curved nature of the release rate profile from a drug resinate that is typical of the current art.

EXAMPLE 5

Figure 4:
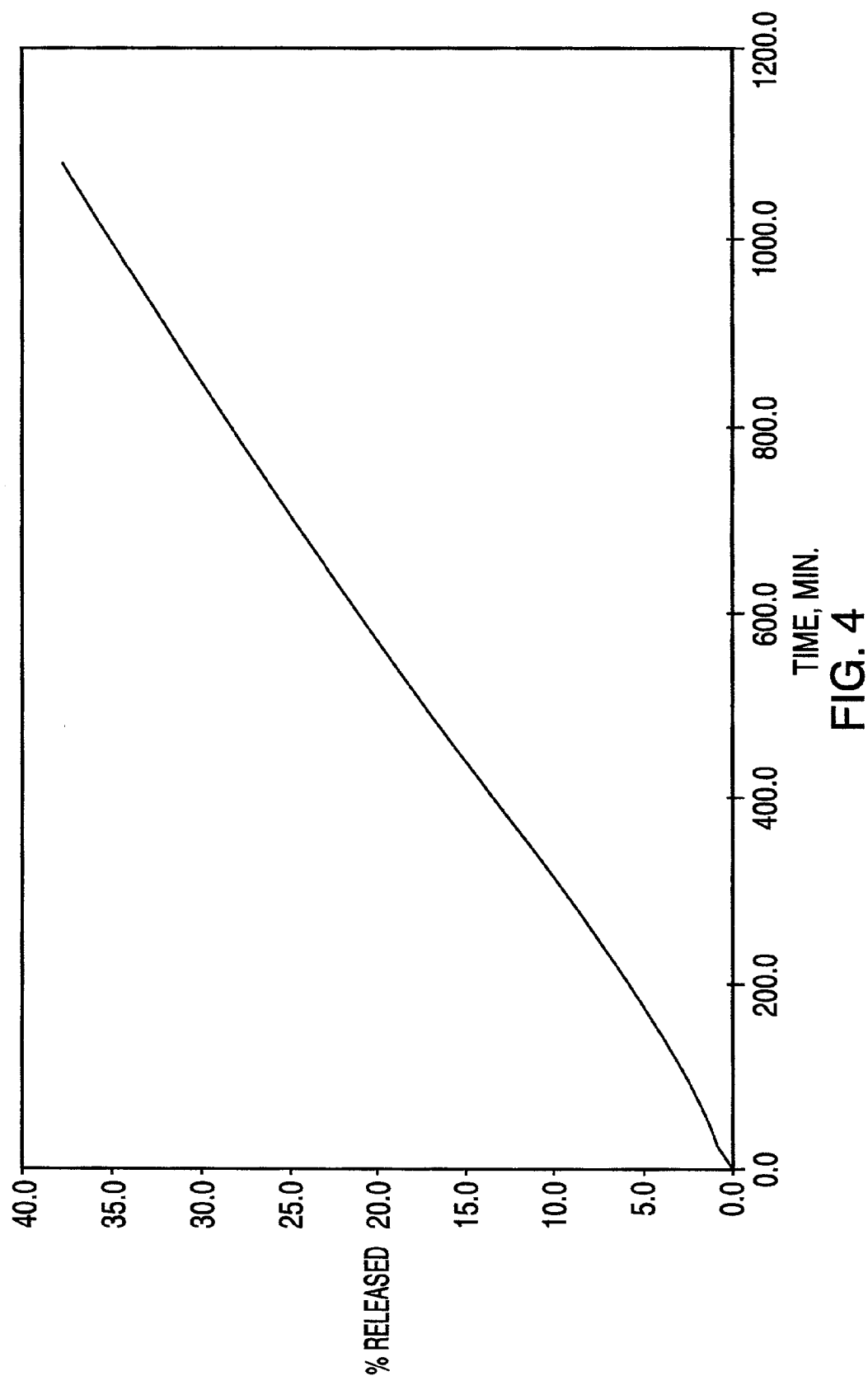
FIG. 4 is a graph showing the release of diclofenac from a combination of the resinate and unloaded cholestyramine based on the data from Example 5.

Release Test on Diclofenac/Cholestyramine Resinate Combined with Unloaded Cholestyramine Resin The experiment described in Example 4 was repeated except that a combination of 127.0 mg of the wet resinate prepared as in Example 3 plus 272.0 mg of unloaded Cholestyramine USP that had been screened to remove particles >37 microns were added to the filtration cell. The flow rate of simulated intestinal fluid was 6.0 ml/min. The results of this example are shown in FIG. 4 expressed as % diclofenac sodium released. This example demonstrates the approximately constant release rate achievable with the present invention.

EXAMPLE 6

Figure 5:
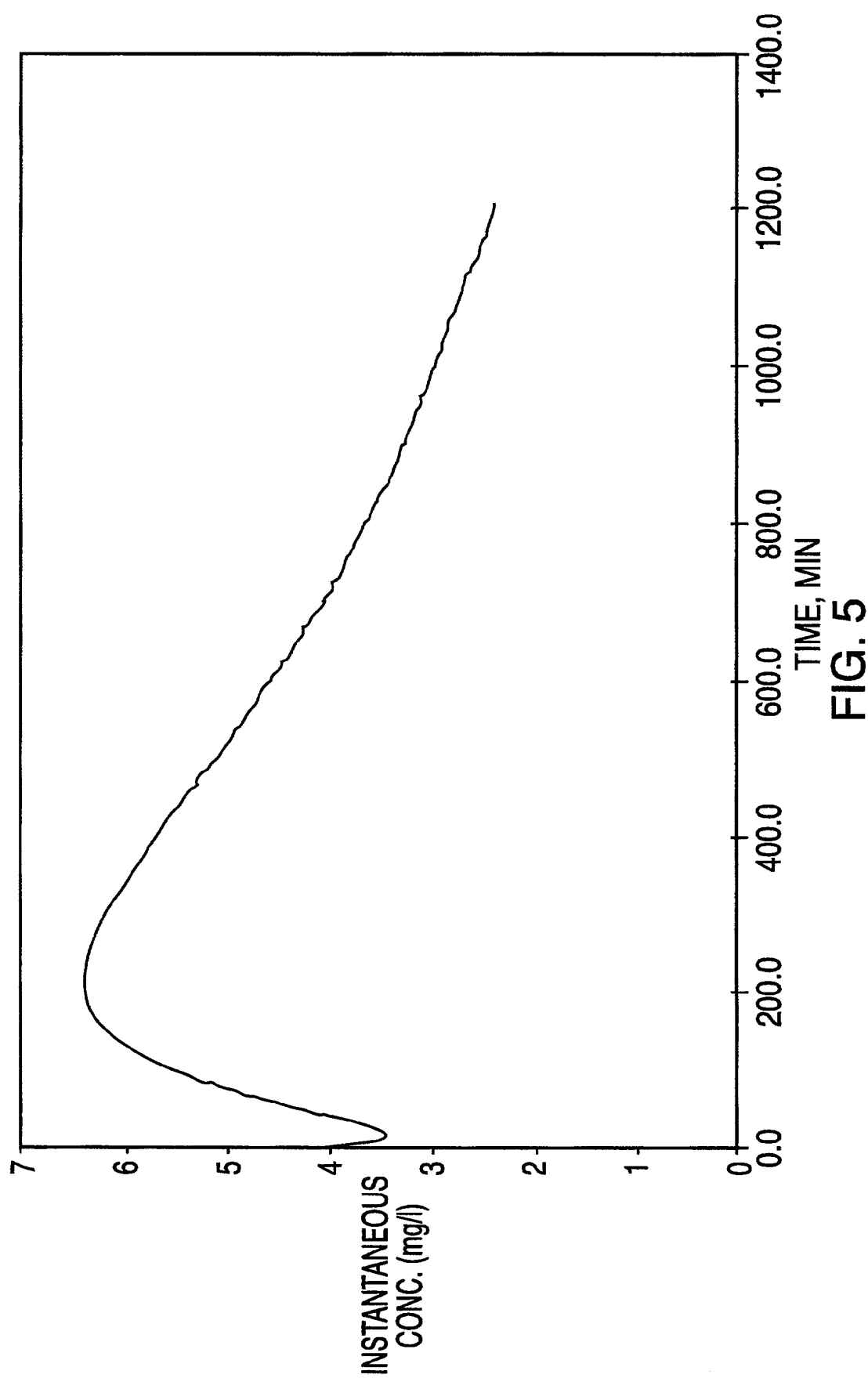
FIG. 5 is a graph showing the release of diclofenac from a combination of the resinate and unloaded cholestyramine based on the data from Example 6.

Release Test on Diclofenac/Cholestyramine Resinate Combined with Unloaded Cholestyramine Resin The experiment described in Example 4 was repeated except that a combination of 126.6 mg of the wet resinate prepared as in Example 3 plus 152.4 mg of unloaded Cholestyramine USP that had been screened to remove particles >37 microns were added to the filtration cell. The flow rate of simulated intestinal fluid was 6.0 ml/min. The results of this example are shown in FIG. 5 expressed as the instantaneous concentration of diclofenac sodium in the effluent. This example demonstrates the ability of the present invention to delay the maximum in the concentration curve to approximately 200 minutes. Note that when using only resinate (Example 2, FIG. 3) the maximum occured at approximately 10 minutes.

EXAMPLE 7

Release Test on Indomethacin/Cholestyramine Resinate

Figure 6:
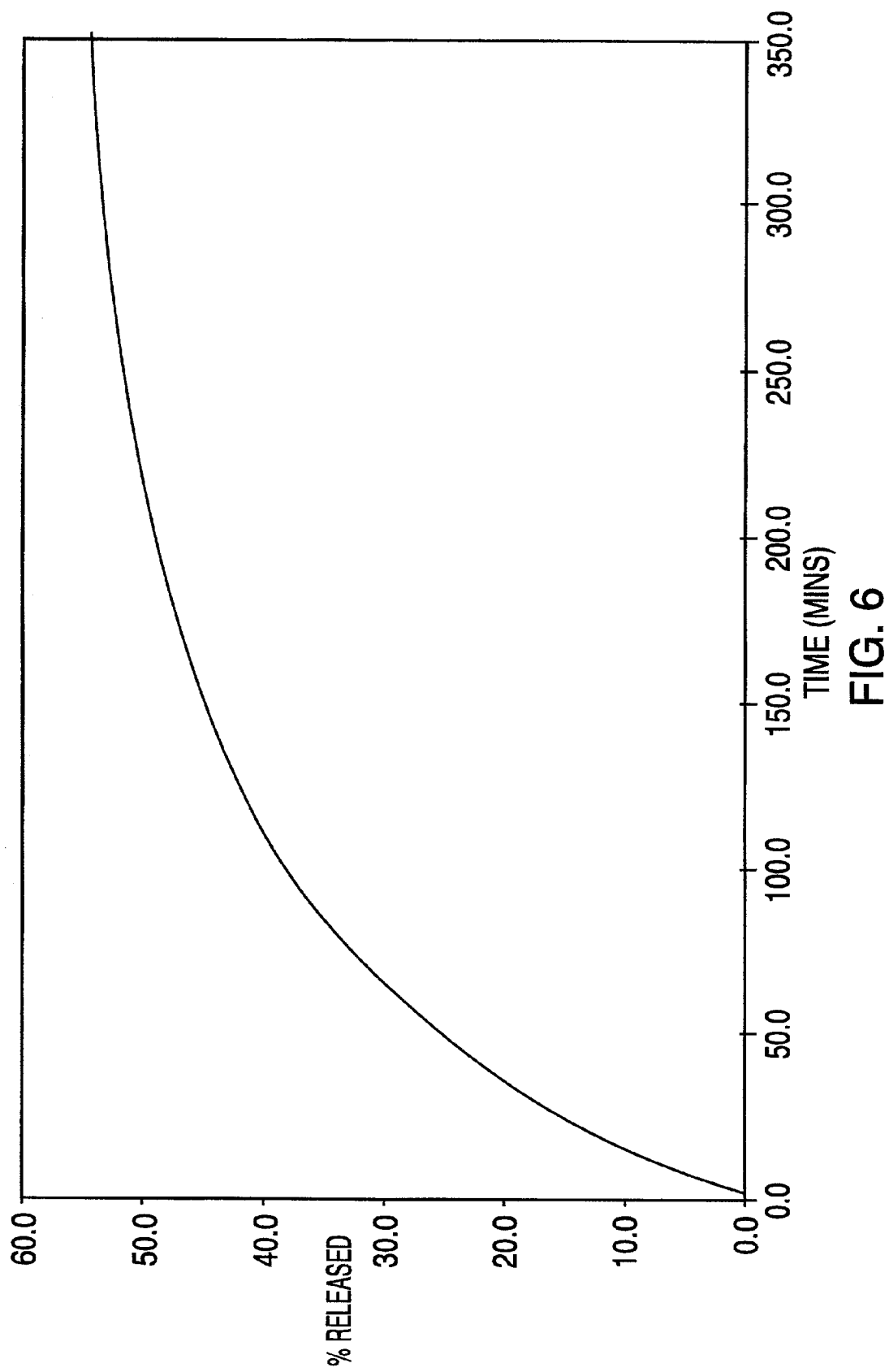
FIG. 6 is a graph showing the release of indomethacin from a resinate based on the data from Example 7.

The experiment described in Example 4 was repeated except that 90.6 mg of a wet resinate prepared in a manner similar to that in Example 2 (drug loading 0.176 g/g wet resinate) was added to the filtration cell. The flow rate of simulated intestinal fluid was 6.3 ml/min. The results of this example are shown in FIG. 6 expressed as the % indomethacin released. The example illustrates the curved nature of the release rate profile from a drug resinate that is typical of the current art.

EXAMPLE 8

Figure 7:
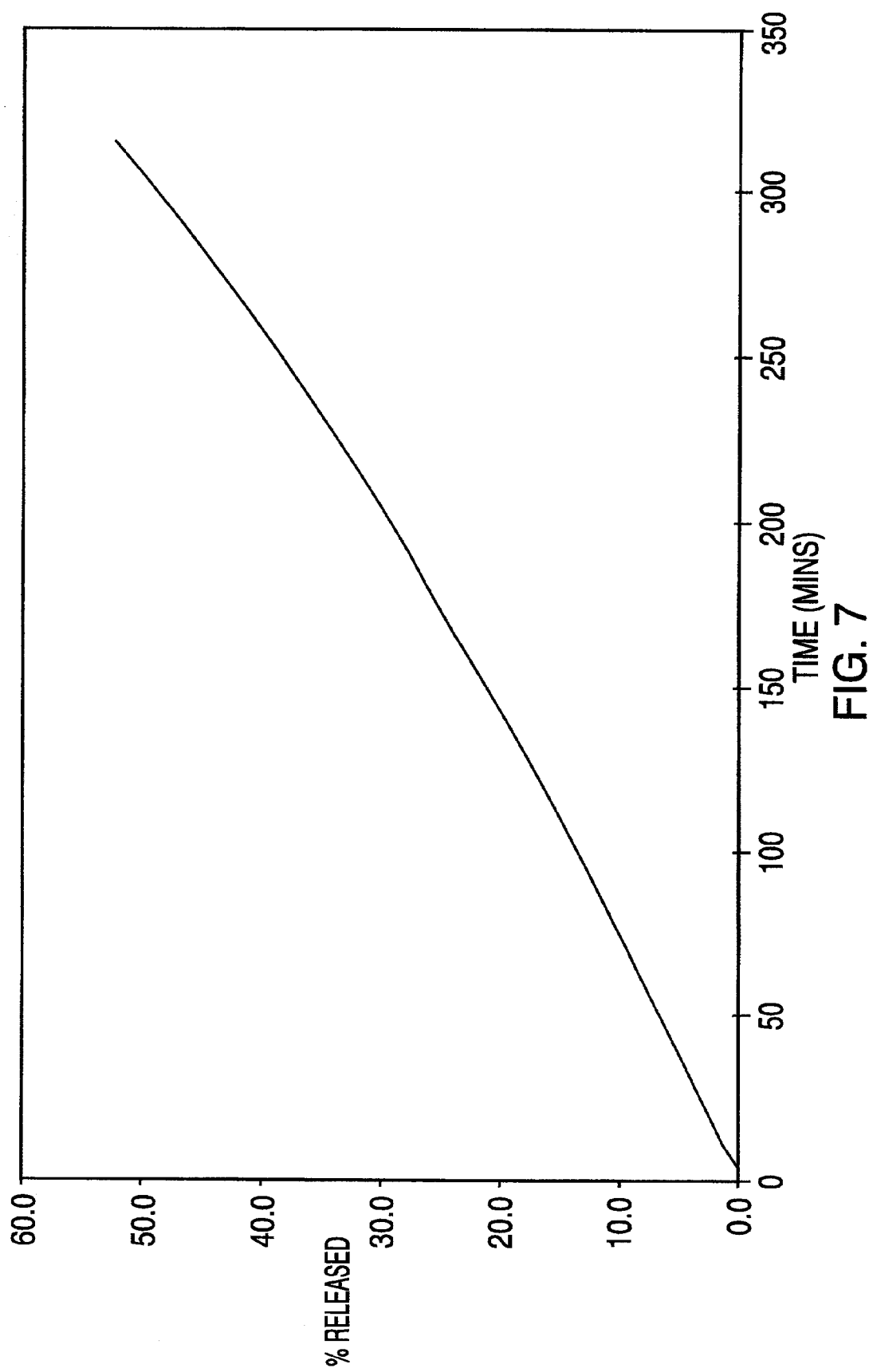
FIG. 7 is a graph showing the release of indomethacin from a combination of the resinate and unloaded cholestyramine based on the data from Example 8.

Release Test on Indomethacin/Cholestyramine Resinate Combined with Unloaded Cholestyramine Resin The experiment described in Example 4 was repeated except that a combination of 117.8 mg of the wet resinate prepared as in Example 2 plus 86.7 mg of of unloaded Cholestyramine USP were added to the filtration cell. The fluid used in the test was a phosphate buffer prepared as described below The flow rate was 6.4 ml/min. The results of this example are shown in FIG. 7 expressed as the % indomethacin released. This example demonstrates the ability of the present invention to create profiles in which the release rate increases gradually over several hours.

Preparation of simulated intestinal fluid: a solution of 6.8 g/l potassium dihydrogen phosphate in deionized water was prepared and sufficient 0.2 mol/l sodium hydroxide solution was added to achieve a pH of 7.5.

Preparation of phosphate buffer solution: Phosphate buffer pH7.2 was prepared as described in the US Pharmacopeia 24, pages 2231–2. One volume of this solution was then diluted with four volumes of deionized water.

We claim:

1. A dosage form comprising: an active ingredient/ion exchange resin complex, in which said ion exchange resin in said complex is at least one of a styrenic strongly acidic cation exchange resin with a sulfonic acid functionality with a weight capacity of 0.1 to 8 meq/g and an acrylic or methacrylic weakly acidic cation exchange resin with a carboxylic acid functionality with weight capacity of 0.1 to 14 meq/g; and, an unloaded cation ion exchange resin which is at least one of a styrenic strongly acidic cation exchange resin with a sulfonic acid functionality with a weight capacity of 0.1 to 8 meq/g and an acrylic or methacrylic weakly acidic cation exchange resin with a carboxylic acid functionality with weight capacity of 0.1 to 14 meq/g; wherein a ratio of unloaded cation exchange resin to said complex is from 0.01:1 to 99:1.

2. A dosage form comprising: an active ingredient/ion exchange resin complex, in which said ion exchange resin in said complex is at least one of a styrenic strongly basic anion exchange resin with a quaternary amine functionality with weight capacity of 0.1 to 6 meq/g and an acrylic anion exchange resin with a tertiary amine functionality with weight capacity of 0.1 to 12 meq/g; and, an unloaded anion ion exchange resin which is at least one of a styrenic strongly basic anion exchange resin with a quaternary amine functionality with weight capacity of 0.1 to 6 meq/g and an acrylic anion exchange resin with a tertiary amine functionality with weight capacity of 0.1 to 12 meq/g; wherein a ratio of unloaded anion exchange resin to said complex is from 0.01:1 to 99:1.

3. A method of manufacturing a dosage form, comprising: creating said dosage form by either:

a. adding an active ingredient/ion exchange resin complex, in which said ion exchange resin in said complex is at least one of a styrenic strongly acidic cation exchange resin with a sulfonic acid functionality with a weight capacity of 0.1 to 8 meq/g and an acrylic or methacrylic weakly acidic cation exchange resin with a carboxylic acid functionality with weight capacity of 0.1 to 14 meq/g, to an unloaded cation ion exchange resin which is at least one of a styrenic strongly acidic cation exchange resin with a sulfonic acid functionality with a weight capacity of 0.1 to 8 meq/g and an acrylic or methacrylic weakly acidic cation exchange resin with a carboxylic acid functionality with weight capacity of 0.1 to 14 meq/g; or, b. adding an active ingredient/ion exchange resin complex, in which said ion exchange resin in said complex is at least one of a styrenic strongly basic anion exchange resin with a quaternary amine functionality with weight capacity of 0.1 to 6 meq/g and an acrylic anion exchange resin with a tertiary amine functionality with weight capacity of 0.1 to 12 meq/g, to an unloaded anion ion exchange resin which is at least one of a styrenic strongly basic anion exchange resin with a quaternary amine functionality with weight capacity of 0.1 to 6 meq/g and an acrylic anion exchange resin with a tertiary amine functionality with weight capacity of 0.1 to 12 meq/g.

4. The method of claim 3 further comprising coating the unloaded ion exchange resin with a permeable membrane to modulate the release rate and/or absorption rate of said active ingredient from said dosage form into a release medium.

5. The method of claim 3 further comprising coating the resinate with a permeable membrane to modulate the release rate and/or absorption rate of said active ingredient from said dosage form into a release medium.

6. The method of claim 3 further comprising coating the unloaded resin and/or resinate with a non-permeable membrane that dissolves at the site where release and absorption are desired.

7. The dosage form of claim 1 in which said ratio of unloaded cation exchange resin to said complex is from 0.1:1 to 10:1, and the active ingredient/ion exchange resin complex is loaded to 1–100% ion exchange capacity of the resin.

8. The dosage form of claim 2 in which said ratio of unloaded anion exchange resin to said complex is from 0.1:1 to 10:1, and the active ingredient/ion exchange resin complex is loaded to 1–100% ion exchange capacity of the resin.

9. The dosage form of claim 7 in which the active ingredient/ion exchange resin complex is loaded to 5–95% ion exchange capacity of the resin.

10. The dosage form of claim 8 in which the active ingredient/ion exchange resin complex is loaded to 5–95% ion exchange capacity of the resin.

11. The method of claim 3 in which a ratio of unloaded ion exchange resin to said complex is from 0.1:1 to 10:1, and said complex is loaded to 1–100% ion exchange capacity of the resin.

12. The method of claim 11 in which said complex is loaded to 5–95% ion exchange capacity of the resin.

* * * * *